United States Patent [19]

Joslyn

[11] 3,982,893

[45] Sept. 28, 1976

[54] STERILIZER CONTROL METHOD AND APPARATUS

[75] Inventor: Larry James Joslyn, Walworth, N.Y.

[73] Assignee: Sybron Corporation, Rochester, N.Y.

[22] Filed: Sept. 8, 1975

[21] Appl. No.: 611,397

[52] U.S. Cl. ............................................ 21/2; 21/93; 21/103; 23/230 B; 23/253 R
[51] Int. Cl.² ........................ A61L 3/02; G01N 25/56
[58] Field of Search .......... 23/230 B, 253 R, 254 R; 21/2, 103, 94, 93

[56] References Cited
UNITED STATES PATENTS

| | | | |
|---|---|---|---|
| 3,450,489 | 6/1969 | Fay | 21/103 X |
| 3,571,563 | 3/1971 | Shulz | 21/94 |
| 3,598,517 | 8/1971 | Beecher | 21/103 |
| 3,861,875 | 1/1975 | Joslyn | 21/103 |

*Primary Examiner*—R.E. Serwin
*Attorney, Agent, or Firm*—Theodore B. Roessel; Roger Aceto

[57] ABSTRACT

A signal generating and transmitting device is disclosed which can be placed within a load to be sterilized to continuously monitor sterilization affecting conditions at the center of the load. Radio signals representing the sensed conditions are transmitted by the device to an antenna in the sterilizing chamber, the antenna in turn being directly wired to a receiver outside the device which adapts these signals for controlling the operation of the sterilizer.

8 Claims, 3 Drawing Figures

3,982,893

STERILIZER CONTROL METHOD AND APPARATUS

BACKGROUND OF THE INVENTION

The present invention relates generally to sterilization control and more particularly to a device which may be placed within the sterilizing chamber for continuously monitoring the various sterilization affecting environmental conditions within the chamber and using the information generated by such device to control the operation of the sterilizer.

In the operation of sterilizing apparatus one of the primary problems involved in achieving sterility results from the inability to accurately monitor the sterilization affecting environmental conditions within the sterilizing chamber and more importantly, within the pack or articles being sterilized. Consequently, simulated load delays or extra sterilizing time are among the various techniques which have been employed to compensate for delays in the heat up time or moisturizing or penetration of the sterilizing gas into the article being sterilized. None of these techniques however, accurately reflect the actual load condition, that is, the conditions within or at the center of the load being sterilized.

The present invention overcomes these difficulties by providing sensor elements and a radio transmitter in a housing which can be placed in the sterilizing chamber, and even within the pack to be sterilized. The sensor elements monitor the various sterilization affecting environmental conditions and the transmitter conveys such information to an antenna which is hard wired through the sterilizer wall to the sterilizer control apparatus outside of the sterilizing chamber.

SUMMARY OF THE INVENTION

The present invention may be characterized in one aspect thereof by the provision of a miniature RF transmitter and an analog to digital converter enclosed in a housing, the housing being made of a material able to withstand the environmental conditions within the sterilizing chamber; an antenna for the transmitter incorporated into the wall of the housing; a plurality of sensors on the exterior of the housing and electrically connected through the housing wall to the converter, each sensor being capable of continuously monitoring a different sterilization affecting environmental condition and the converter converting the information received from the sensors to a digital signal; the RF generator transmitting the digital signal to a receiving antenna in the sterilizer; and a receiver outside of the sterilizer and hard wired to the receiving antenna for utilizing the transmitted information to control and/or monitor the sterilizer operation.

OBJECTS OF THE INVENTION

An object of the present invention is to provide means for continuously monitoring a plurality of environmental conditions within the sterilizing chamber.

Another object of the present invention is to provide a RF transmitter for location within the sterilizing chamber which is capable of continuously transmitting signals which are representative of the changing environmental conditions within the chamber.

A further object of the present invention is to provide sensor and transmitter means located within a sterilizing chamber for continuously monitoring the sterilization affecting environmental conditions within the chamber and emitting radio frequency signals representative of such condition.

These and other objects, advantages and characterizing features of the present invention will become more apparent upon consideration of the following detailed description thereof when taken in connection with the accompanying drawing depicting the same.

DESCRIPTION OF THE PREFERRED EMBODIMENTS

Figure 1:
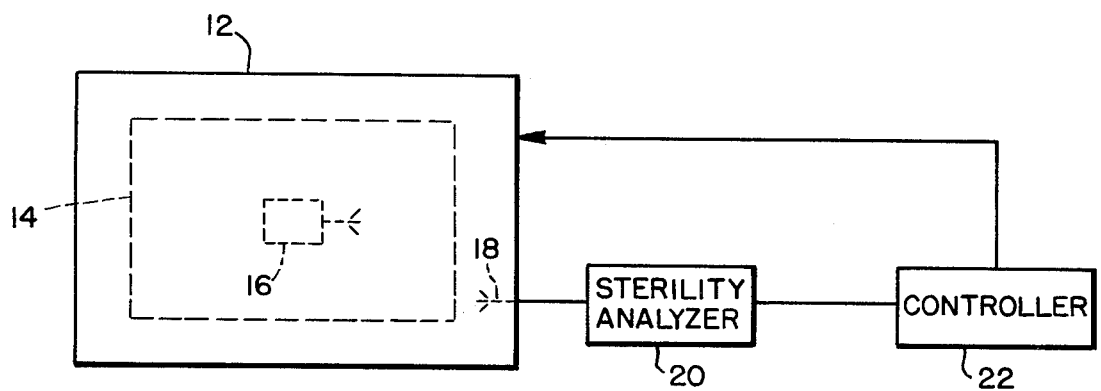
FIG. 1 is a schematic view showing a sterilizing system employing the radio transmitting device of the present invention.

Referring to the drawings, FIG. 1 shows a sterilizer indicated at 12. It should be appreciated that reference numeral 12 is meant to include the sterilizing vessel together with the various connections for steam and/or gas and the control means such as a timer for controlling the operations of the sterilizer all of which are standard and well-known in the art. A load to be sterilized is placed within the sterilizing chamber and is indicated by the reference numeral 14. Placed within the load to be sterilized is the environment monitor and RF transmitter of the present invention 16. Within the sterilizer is an antenna 18 which is directly wired through the wall of the sterilizer to a sterility analyzer 20. The analyzer, in turn, is connected to a sterilizer controller 22 which can operate the various valves timers, vacuum pumps, etc. for controlling the operation of sterilizer 12.

Figure 2:
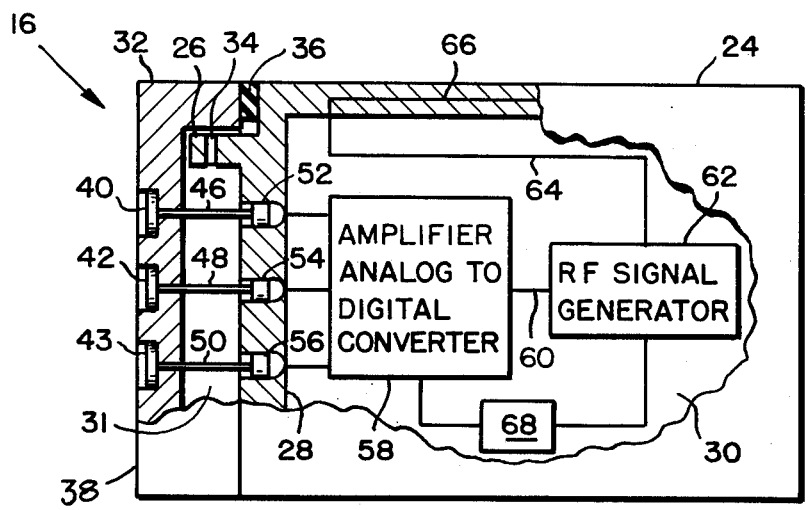
FIG. 2 is a schematic view partly broken away and in section of the device according to the present invention incorporating sensor and transmitter means.

FIG. 2 shows the monitor-transmitter 16 of the present invention to include a housing 24 having a neck portion 26. The neck portion is sealed by a wall 28 to create a closed chamber 30 within the housing.

The second chamber 31 is defined by a neck portion 26, wall 28 and a cap member 32. Cap 32 is preferably installed over neck 26 in a vacuum environment so as to lock onto housing 24 as exterior pressure is increased. For this purpose, the neck portion is provided with a vent bore 34 so that when the cap is placed on the neck portion and the exterior pressure reduced the air in chamber 32 will be evacuated through vent bore 34. This seats the cap tightly against a seal member 36 disposed between the cap and the housing. Once the cap is sealed in the fashion, returning the housing to atmospheric pressure will force the cap against the housing and maintain the negative pressure or vacuum environment in chamber 31.

Carried on the exterior surface 38 of cap 32 are a plurality of sensing members 40, 42, and 43. These sensors are of the type well known in the art and are capable of translating a particular environmental condition into a representative electrical signal such as a voltage or current. Any change in the condition will then produce a corresponding voltage or current change, so that a continuous monitoring of the environment is possible. For example, sensor 40 can be a lithum chloride button. Lithium chloride is known to change its electrical resistances in direct proportion to humidity. Accordingly, as shown in FIG. 2, sensor 40 would provide an electrical signal representative of the humidity in the environment to which the sensor is exposed.

Sensor 42 may be any of the well-known materials which exhibit a change in electrical resistance responsive to the pH of the environment to which it is exposed. In this way, for example, the resistance of sensor 42 could be used as a means to indicate the concentration of a pH affecting sterilizing gas such as ethylene oxide.

Sensor 43 may be any suitable thermocouple for sensing the temperature of the environment to which it is exposed.

Extending from each of the sensors are pins 46, 48 and 50 respectively. These pins are in turn adapted to mate with pin sockets 52, 54 and 56 contained in wall member 18. It is via these pin connections that the input signals from the sensors are carried to an amplifier and analog to digital converter 58 located within chamber 20. Converter 58 is a device well known in the art and it is sufficient for the present invention merely to say that it is a device which converts a continuous electrical signal to a digital signal, that is, it converts a function of continuous variable to a representative number sequence. The output 60 of the converter is then used to modulate the radio frequency of an RF signal generator 62. The modulated signal from the generator is fed through lead wire 64 to an antenna 66 in the housing wall.

Completing the device is a power supply means 68 to operate both the digital converter and the generator. While a separate power supply means has been shown, it might also be possible to utilize the energy produced by the thermocouple 43 or a separate thermocouple to power the converter and generator.

Figure 3:
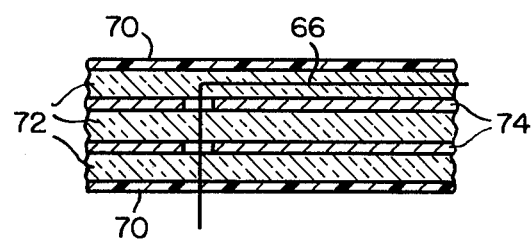
FIG. 3 is a view on an enlarged scale showing a portion of the wall of the device in cross section.

The material of the housing and cap must be such that the converter 58 and RF generator 62 are protected from the adverse environmental conditions within the sterilizer, particularly, the temperature conditions. For this purpose FIG. 3 shows a section of a wall of the housing to be a laminated structure consisting of outer and inner layers 70 of a temperature resistant plastic. Between layers 70 are multiple layers 72 of a glass fiber insulation. The layers of insulation are in turn separated by sheets of aluminum reflective shielding 74. As shown in FIG. 3, the antenna 66 is incapsulated in the outer most layer of glass fiber.

In addition to the material of the housing and end cap, the converter and RF generator are further protected from the environment of the sterilizer by evacuating chamber 30 so as to have these elements located in a partial vacuum. The end cap 32, the partial vacuum of chamber 31 and the wall 18 further insulates the internal components from the environment so that the only major thermal conduction routes is via the thin wires 46, 48 and 50 which convey the electrical signals from the exterior of housing to the converter.

In operation, then, the device 16 of the present invention is simply wrapped with or placed within one or more of the goods 14 to be sterilized and the goods placed within the sterilizing chamber 12. During the sterilizing cycle, device 16 will indicate the environment conditions existing at the heart of the load to be sterilized. The signals eminating from the device are received by the receiving antenna 18 which in turn conveys the information to the sterility indicator 20 and from there to the sterilizer controller 22. Sterility indicator 20 may be of the type described in U.S. Pat. No. 3,861,875. The sterility indicator and sterilizer control may delay the start of the timed sterilizing period until such time as the conditions at the heart of the load as indicated by device 16 are in the proper limits for sterilization. Should the environmental conditions device vary, device 16 will sense and transmit the information so that the sterility analyzer and controller can make the necessary adjustments in the sterilizer environment to bring the conditions back within proper limits. Since the conditions at the most difficult place to sterilize, namely, the center of the load, are directly monitored it can be safely assumed that the entire load is exposed to the optimum conditions for sterilization.

Thus, it should be appreciated that the present invention accomplishes its intended objects in providing a means for continuously monitoring a plurality of sterilization affecting environmental conditions at the heart or core of the load to be sterilized and adjusting them accordingly to maintain the optimum sterilizing conditions. The monitor-transmitter device 16 is relatively small and can be incorpoated into the goods to be sterilized and that no separate sensors with artifical barriers need be provided.

Having thus described the invention in detail what is claimed as new is:

1. Sterilizer control apparatus comprising:
   a. a housing enclosing a sealed chamber, said housing adapted to be included within a load to be sterilized;
   b. sensor means on the exterior of a wall of said housing for continuously monitoring a plurality of sterilization affecting environmental conditions within said load when said load is within a sterilizing chamber, said means including at least an element whose electrical resistance changes in proportion to humidity and a thermocouple, said means being capable of generating a continuous sensor signal which varies in response to changes in each of said environment conditions;
   c. an RF generator in said housing for generating a radiated RF signal which is modulated in response to said sensor signal;
   d. a receiving antenna within said sterilizing chamber remote from the load being sterilized for receiving the radiated RF signal from said RF generator; and
   e. control means outside of said sterilizer in electrical communication with said receiving antenna for utilizing the information contained in said radiated RF signal to control the operation of said sterilizer.

2. Sterilizer control apparatus as in claim 1 wherein said housing includes a body portion having a necked end, the necked end being sealed by a wall so as to provide a closed chamber for housing said RF generator.

3. Sterilizer control apparatus as in claim 2 wherein said chamber is partly evacuated for heat insulation purposes.

4. Sterilizer control apparatus as in claim 2 including a cap over said necked end, said sensor means being on said cap, said cap, wall and necked end defining a second closed chamber, said sensor means having pins and said wall having pin sockets so that placing said cap on said necked end mates said pins and pin sockets to provide an electrical path through said second chamber, said converter means being in electrical communication with said pin sockets.

5. Sterilizer control apparatus as in claim 4 including a gasket between said cap and necked end and a vent opening in said necked end to premit the evacuation of said second chamber and the sealing of said cap to said necked end.

6. Sterilizer control apparatus as in claim 1 wherein said housing is constructed of a heat insulating laminate and a transmitting antenna for said RF generator embedded in said laminate.

7. Sterilizer control means as in claim 1 including;
   a. converter means within said housing having its input in electrical contact with said sensor means for converting said continuous electrical signal to a digital signal; and
   b. said RF generator being in electrical contact with the output of said converter, said RF signal being modulated in response to said digital signal.

8. A method for controlling the operation of a sterilizer comprising the steps of:
   a. placing RF radiating means within a load to be sterilized and then placing the load into a sterilizing chamber;
   b. continuously monitoring a plurality of sterilizing affecting environmental conditions within the sterilizing chamber including at least humidity and temperature by sensor means located within the load, the sensor means being capable of issuing a continuous sensor signal which is representative of each of the sensed conditions;
   c. modulating the RF signal of said radiating means in response to said sensor signal;
   d. conveying said modulated RF signal outside of said sterilizing chamber; and
   e. operating a sterilizer control means responsive to the modulated RF signal conveyed to the outside of said sterilizing chamber.

* * * * *